(12) United States Patent
Moriarty et al.

(10) Patent No.: US 6,700,025 B2
(45) Date of Patent: Mar. 2, 2004

(54) PROCESS FOR STEREOSELECTIVE SYNTHESIS OF PROSTACYCLIN DERIVATIVES

(75) Inventors: Robert M. Moriarty, Oak Park, IL (US); Hitesh Batra, Chicago, IL (US)

(73) Assignee: United Therapeutics Corporation, Washington, DC (US)

( * ) Notice: Subject to any disclaimer, the term of this patent is extended or adjusted under 35 U.S.C. 154(b) by 0 days.

(21) Appl. No.: 09/754,107

(22) Filed: Jan. 5, 2001

(65) Prior Publication Data

US 2002/0099034 A1 Jul. 25, 2002

(51) Int. Cl.$^7$ .................. C07C 39/12; C07C 33/34; C07C 261/00; C07D 265/30; C07D 211/06
(52) U.S. Cl. .................. 568/734; 568/807; 568/808; 544/154; 544/171; 544/176; 544/376; 546/203; 546/309; 548/250; 560/28; 560/56; 52/446
(58) Field of Search .................. 568/734, 807, 568/808, 633; 544/154, 171, 176, 376; 546/203, 309; 548/250; 560/56, 28; 562/466; 566/172

(56) References Cited

U.S. PATENT DOCUMENTS

| | | | |
|---|---|---|---|
| 4,306,075 A | * 12/1981 | Aristoff | .................. 560/56 |
| 5,153,222 A | 10/1992 | Tadepalli et al. | |
| 6,441,245 B1 | 8/2002 | Moriarty et al. | |

FOREIGN PATENT DOCUMENTS

| | | | |
|---|---|---|---|
| EP | 0 087 237 A1 | | 8/1983 |
| WO | WO 98/39337 | | 9/1998 |
| WO | 99/21830 | * | 5/1999 |

OTHER PUBLICATIONS

Mulzer et al, Liebigs.Ann.Chem., 891–897 (1988).*
Belch et at, "Randomized, Double–Blind, Placebo–Controlled Study Evaluating the efficacy and Safety of AS–013, a Prostaglandin E$_1$ Prodrug, in Patients With Intermittent Claudication," Circulation, vol. 95, No. 9, American Heart Association Inc., pp. 2298–2302; May 6, 1997.
Nelson, "Prostaglandin Nomenclature," Journal of Medicinal Chemistry, vol. 17, No. 9, American Chemical Society, pp. 911–918, Sep. 1974.
Takano et al., "Enantiodivergent Synthesis of Both Enantiomers of Sulcatol and Matsutake Alcohol from (R)–Epichlorohydrin," Chemistry Letters, The Chemical Society of Japan, pp. 2017–2020, 1987.

Mathre et al., "A Practical Enantioselective Synthesis of α,α–Diaryl–2–Pyrrolidinemethanol, Preparation and Chemistry of the Corresponding Oxazaborolidines," J. Org. Chem., vol. 56 No. 2, American Chemical Society, pp. 751–752, 1991.
Pagenkopf, "Substrate and Reagent Control of Diastereoselectivity in Transition Metal–Mediated Process: Development of a Catalytic Photo Promoted Pauson–Khand Reaction," Caplus 1999, Abstract XP–002097925.
Khand et al., "Organocobalt Complexes. Part II. Reaction of Acetylenehexacarbonyldicobalt Complexes, $(R^1C_2R^2)Co_2(CO)_6$, with Norbornene and its Derivatives," J. Chem. Soc., J.C.S. Perkin I., pp. 977–981, 1963.
Pauson, "A Convenient and General Route to a Wide Range of Cyclopentenone Derivatives," Tetrahedron, vol. 41, No. 24, Pergamon Press Ltd., pp. 5855–5860, 1985.
Schore, "Transition–Metal–Medicated Cycloaddition Reactions of Alkynes in Organic Synthesis," Chem. Rev., vol. 88, American Chemical Society, pp. 1081–1119, 1988.
Shambayati et al., "N–Oxide Promoted Pauson–Khand Cyclizations at Room Temperature," Tetrahedron Letters, vol. 31 No. 37, Pergamon Press, pp. 5289–5292, 1990.
Jeong et al., "Catalytic Version of the Intramolecular Pauson–Khand Reaction," J. Am. Chem. Soc., vol. 116, American Chemical Society, pp. 3159–3160, 1994.
Chung et al., "Promoters for the (Alkyne) hexacarbonyldicobalt–Based Cyclopentenone Synthesis," Organometallics, vol. 12, American Chemical Society, pp. 220–223, 1993.
Hicks et al., "A Practical Titanium–Catalyzed Synthesis of Bicyclic Cyclopentenones and Allylic Amines," J. Org. Chem., vol. 61 No. 8, pp. 2713–2718, 1996.
Zhang et al. "A Nickel(O)–Catalyzed Process for the Transformation of Enynes to Bicyclic Cyclopentenones," J. Org. Chem., vol. 61 No. 14, pp. 4498–4499, 1996.
Pagenkopf et al., "Photochemical Promotion of the Intramolecular Pauson–Khand Reaction. A New Experimental Protocol for Cobalt–Catalyzed [2+2+1] Cycloadditions," J. Am. Chem. Soc., vol. 118 No. 9, American Chemical Society, pp. 2285–2286, 1996.

* cited by examiner

*Primary Examiner*—Johann Richter
*Assistant Examiner*—Sikarl A. Witherspoon
(74) *Attorney, Agent, or Firm*—Foley & Lardner

(57) ABSTRACT

An improved method is described for making 9-deoxy-PGF$_1$-type compounds. In contrast to the prior art, the method is stereoselective and requires fewer steps than the known methods for making these compounds.

13 Claims, No Drawings

PROCESS FOR STEREOSELECTIVE SYNTHESIS OF PROSTACYCLIN DERIVATIVES

FIELD OF THE INVENTION

The present application relates to a shortened process for producing prostacyclin derivatives and novel intermediate compounds useful in the process. The present application also relates to stereoselectively produced compounds prepared by the inventive process. Furthermore, the prostacyclins produced in this process are pure diastereomers, i.e., >99%.

BACKGROUND OF THE INVENTION

Prostacyclin derivatives are useful pharmaceutical compounds possessing activities such as platelet aggregation inhibition, gastric secretion reduction, lesion inhibition, vasodilation and bronchodilation.

For convenience, the novel prostacyclin derivatives will be referred to by the trivial, art-recognized system of nomenclature described by N. A. Nelson, J. Med. Chem. 17:911 (1974) for prostaglandins. Accordingly, all of the novel prostacyclin derivatives herein will be named as 9-deoxy-$PGF_1$-type compounds.

U.S. Pat. No. 4,306,075 discloses methods for making prostacyclin derivatives. However, these and other known processes involve a large number of steps. It is an object of the present invention to provide an improved method of preparing prostacyclin derivatives involving fewer steps.

SUMMARY OF THE INVENTION

The present invention relates to a process for preparing 9-deoxy-$PGF_1$-type compounds by a process that is stereoselective and requires fewer steps than the prior art. The invention also relates to novel intermediates prepared during the synthesis of the 9-deoxy-$PGF_1$-type compounds. Furthermore, the invention relates to 9-deoxy-$PGF_1$-type compounds prepared by the inventive process.

DETAILED DESCRIPTION OF THE PREFERRED EMBODIMENTS

In one embodiment, the present invention relates to an improved stereoselective method for making 9-deoxy-$PGF_1$-type compounds comprising converting a compound of the formula:

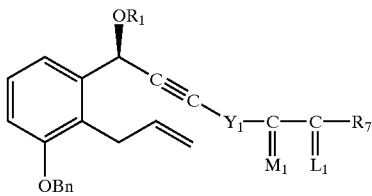

into a compound of the following formula:

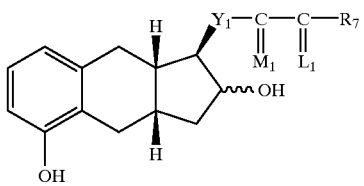

wherein $Y_1$ is trans-CH=CH—, cis-CH=CH—, —$CH_2(CH_2)_m$—, or —C≡C—; m is 1, 2, or 3;

wherein $R_1$ is H or an alcohol protecting group;

wherein $R_7$ is (1) —$C_pH_{2p}$—$CH_3$, wherein p is an integer from 1 to 5, inclusive, (2) phenoxy optionally substituted by one, two or three chloro, fluoro, trifluoromethyl, ($C_1$-$C_3$)alkyl, or ($C_1$-$C_3$)alkoxy, with the proviso that not more than two substituents are other than alkyl, with the proviso that $R_7$ is phenoxy or substituted phenoxy, only when $R_3$ and $R_4$ are hydrogen or methyl, being the same or different, (3) phenyl, benzyl, phenylethyl, or phenylpropyl optionally substituted on the aromatic ring by one, two or three chloro, fluoro, trifluoromethyl, ($C_1$-$C_3$) alkyl, or ($C_1$-$C_3$)alkoxy, with the proviso that not more than two substituents are other than alkyl, (4) cis-CH=CH—$CH_2$—$CH_3$, (5) —$(CH)_2$—CH(OH)—$CH_3$, or (6) —$(CH)_3$—CH=$C(CH_3)_2$;

wherein —$C(L_1)$—$R_7$ taken together is (1) ($C_4$-$C_7$)cycloalkyl optionally substituted by 1 to 3 ($C_1$-$C_5$)alkyl;

(2) 2-(2-furyl)ethyl, (3) 2-(3-thienyl)ethoxy, or (4) 3-thienyloxymethyl;

wherein $M_1$ is α-OH:β-$R_5$ or α-R:β-OH or α-$OR_1$:β-$R_5$ or α-$R_5$:β-$OR_1$, wherein $R_5$ is hydrogen or methyl and $R_1$ is an alcohol protecting group; and wherein $L_1$ is α-$R_3$:β-$R_4$, α-$R_4$:β-$R_3$, or a mixture of α-$R_3$:β-$R_4$ and α-$R_4$:β-$R_3$, wherein $R_3$ and $R_4$ are hydrogen, methyl, or fluoro, being the same or different, with the proviso that one of $R_3$ and $R_4$ is fluoro only when the other is hydrogen or fluoro.

Preferably, the above conversion is carried out through cobalt-mediated cyclization, in which the enyne undergoes intramolecular cyclization accompanied by a carbon monoxide insertion to form the tricyclic structure shown below.

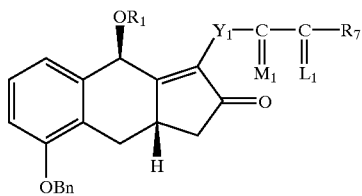

More preferably, this cyclization is carried out by reacting $Co_2(CO)_8$ with a compound of the formula:

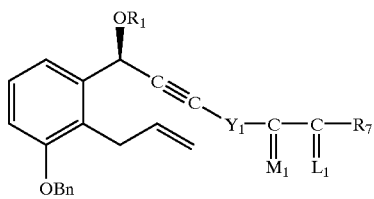

using a suitable non-reactive solvent. Preferably, the non-reactive solvent is a chlorinated solvent, a hydrocarbon solvent, or an aromatic solvent. More preferably, the non-reactive solvent is selected from the group consisting of 1,2-DME (1,2-dimethoxyethane), $CH_2Cl_2$, toluene, isooctane, and heptane.

In the case of carrying out the cobalt-mediated cyclization with 1,2-DME after reacting $Co_2(CO)_8$ with the compound of the formula:

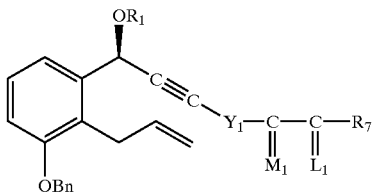

to form a complex with the alkynyl group, preferably the solvent is removed in a subsequent step after intramolecular cyclization occurs to form the tricyclic compound.

Although $Co_2(CO)_8$ contributes a carbonyl during the reaction, it is not necessary to react equal amounts of the starting compound of the above formula and $Co_2(CO)_8$. It is also possible to use the $Co_2(CO)_8$ in a catalytic way, by introducing a relatively small amount of $Co_2(CO)_8$ and also introducing CO into the reaction mixture (e.g., by bubbling CO into the reaction mixture) in the presence of light or heat which causes the transfer of CO through a Co-mediated complex formed with the compound of the formula:

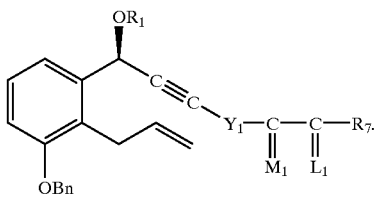

In another preferred embodiment, the present invention relates to an improved stereoselective method for making 9-deoxy-$PGF_1$-type compounds comprising the following reaction with heat or light:

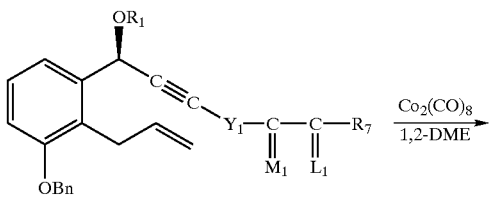

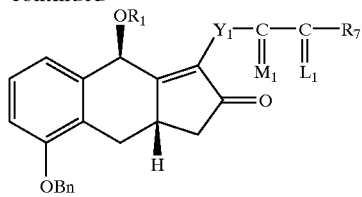

wherein $Y_1$ is trans-CH=CH—, cis-CH=CH—, —$CH_2(CH)_m$—, or —C≡C—; m is 1,2, or 3;

wherein $R_1$ is an alcohol protecting group;

wherein $R_7$ is
(1) —$C_pH_{2p}$—$CH_3$, wherein p is an integer from 1 to 5, inclusive,
(2) phenoxy optionally substituted by one, two or three chloro, fluoro, trifluoromethyl, ($C_1$-$C_3$)alkyl, or ($C_1$-$C_3$)alkoxy, with the proviso that not more than two substituents are other than alkyl, with the proviso that $R_7$ is phenoxy or substituted phenoxy, only when $R_3$ and $R_4$ are hydrogen or methyl, being the same or different,
(3) phenyl, benzyl, phenylethyl, or phenylpropyl optionally substituted on the aromatic ring by one, two or three chloro, fluoro, trifluoromethyl, ($C_1$-$C_3$) alkyl, or ($C_1$-$C_3$)alkoxy, with the proviso that not more than two substituents are other than alkyl,
(4) cis-CH=CH—$CH_2$—$CH_3$,
(5) —$(CH_2)_2$—CH(OH)—$CH_3$, or
(6) —$(CH_2)_3$—CH=C$(CH_3)_2$;

wherein —C($L_1$)—$R_7$ taken together is
(1) ($C_4$-$C_7$)cycloalkyl optionally substituted by 1 to 3 ($C_1$-$C_5$)alkyl;
(2) 2-(2-furyl)ethyl,
(3) 2-(3-thienyl)ethoxy, or
(4) 3-thienyloxymethyl;

$M_1$ is α-OH:β-$R_5$ or α-$R_5$:β-OH or α-$OR_1$:β-$R_5$ or α-$R_5$:β-$OR_1$, wherein $R_5$ is hydrogen or methyl and $R_1$ is an alcohol protecting group;

wherein $L_1$ is α-$R_3$:β-$R_4$, α-$R_4$:β-$R_3$, or a mixture of α-$R_3$:β-$R_4$ and α-$R_4$:β-$R_3$, wherein $R_3$ and $R_4$ are hydrogen, methyl, or fluoro, being the same or different, with the proviso that one of $R_3$ and $R_4$ is fluoro only when the other is hydrogen or fluoro.

The present invention also relates to a method of making the following compounds utilizing the following reaction scheme:

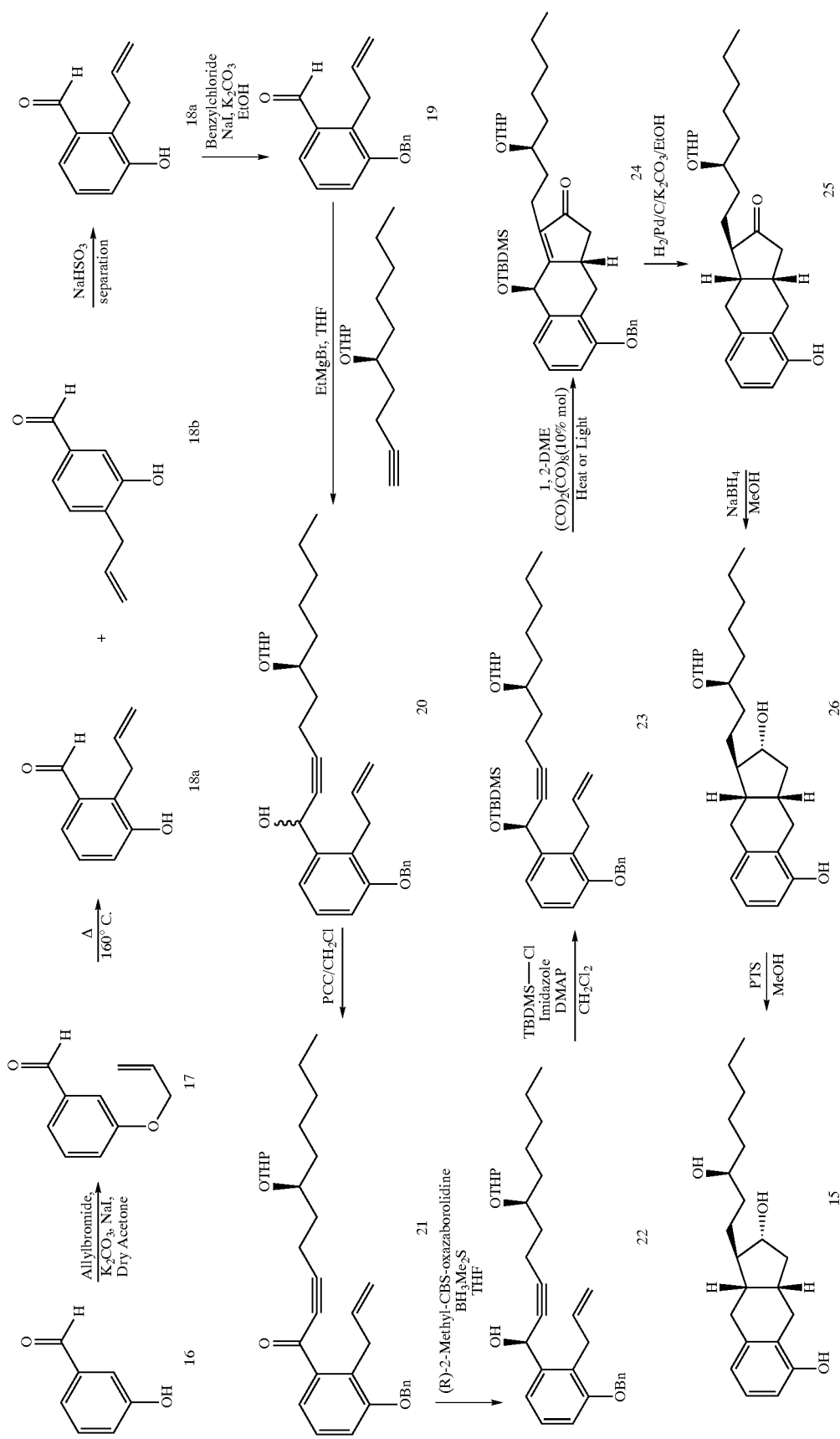

wherein R₁ is in each case an independently selected alcohol protecting group. Preferred alcohol protecting groups are tertiary butyl dimethyl silyl (TBDMS) and tetra hydro pyranyl (THP), trimethylsilyl (TMS), TES or any bulky groups.

The present invention also relates to the following novel intermediate compounds:

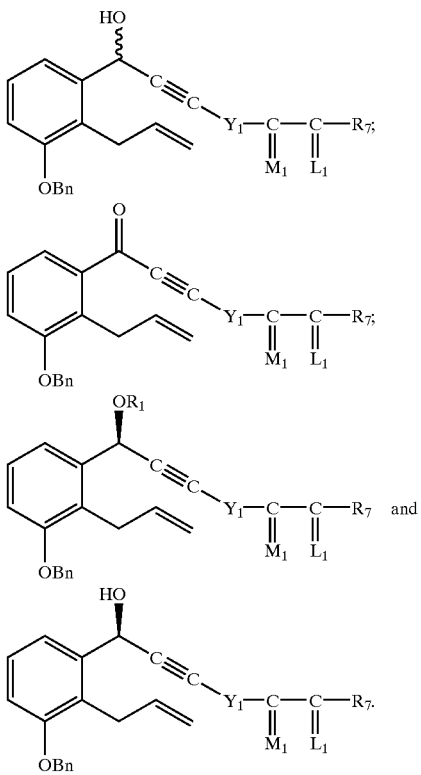

wherein $Y_1$, $M_1$, $L_1$, $R_1$ and $R_7$ are as defined above.

The present invention also relates to a stereoselectively produced compound according to the following formula:

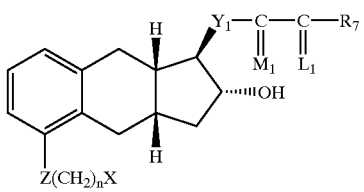

wherein Z is O, S, $CH_2$, or $NR_8$ in which $R_8$ is H, alkyl or aryl;

X is H, CN, $OR_9$, or $COOR_9$ in which $R_9$ is alkyl, THP or TBDMS;

n is 0, 1, 2, or 3;

$Y_1$, $M_1$, $L_1$, and $R_7$ are as defined above and the compound is produced according to the inventive stereoselective synthesis. The produced compounds are diastereomerically pure.

In a preferred embodiment of the stereoselectively produced isomeric compound, Z is O, n is 1, X is COOH, $Y_1$ is —$CH_2CH_2$—$M_1$ is α-OH:β-$R_5$, wherein $R_3$ is hydrogen, $L_1$ is α-$R_3$:β-$R_4$, wherein $R_3$ and $R_4$ are hydrogen and $R_7$ is propyl. The stereoselectively produced isomeric compound is diastereomerically pure.

"Diastereomerically pure, i.e., >99%" means that the present diastereoselective synthesis produces diastereomers as represented by the above formula having >99% purity.

The purity level is determined by running the product through a chiral HPLC column where >99% of the above diastereomer exits the column as a single peak. A diastereoselective or stereoselevtive synthesis involves one or more reactions that yield predominantly one diastereomer or stereoisomer of several possible disatereomers or stereoisomers.

The present invention is further illustrated by, though in no way limited to, the following examples.

EXAMPLES

Preparation of 9-Deoxy-2',9α-methano-3-oxa-4,5,6-trinor-3,7-(1',3'-inter-phenylene)-13,14-dihydro-$PGF_1$ (UT-15)

Preparation of Allylether 17:

(a)

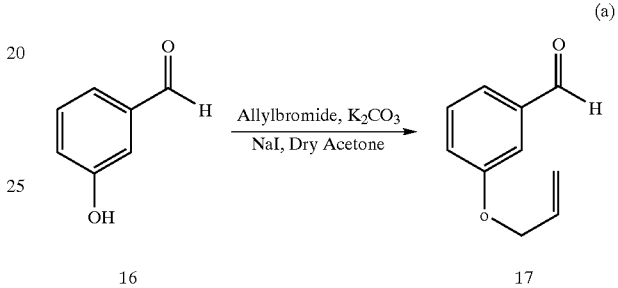

To an oven dry 1 L three-necked round bottom flask fitted with a reflux condenser and mechanical stirrer was added meta hydroxybenzaldehyde (16, 100 gms. 0.819 mol) in 500 ml dry acetone, anhydrous potassium carbonate 226.2 gms (1.6 mol), sodium iodide 12.2 gms (0.081 mol) and allyl bromide 99 ml (1.14 mol). The resulting mixture was refluxed with stirring under an atmosphere of argon for 18–20 hrs, until the reaction was complete (as monitored by thin layer chromatography (TLC), hexane ethyl acetate 4:1). Then the reaction mixture was filtered on a Büchner funnel and the filtrate was evaporated in vacuo to give an oily compound (140 gms) which was dissolved in 500 ml of dichloromethane and washed with 10% NaOH solution (300 ml). The aqueous layer was separated and extracted with 200 ml dichloromethane. The combined organic layers were dried over sodium sulfate and evaporated in vacuo to afford crude allylether 17 (122 gms). The allyl ether was passed through a short column of $SiO_2$ (316 gms) using 1% ethyl acetate in hexanes. Fractions containing compound 17 were evaporated in vacuo to give 17 as a yellow oil, yield 112 gms (84%); b.p 80° C./0.02 mm (lit: (1) b.p 78° C./0.02 mm); ¹HNMR ($CDCl_3$): 4.49–4.52 (d, 2H, ($CH_2$), 5.21–5.41 (m, 2H=$CH_2$), 5.89–6.06 (m, 1H, =CH), 7.08–7.38 (m, 4H, ArH), 9.89 (s, H, CHO).

Claisen Rearrangement of Allylether 17:

(b)

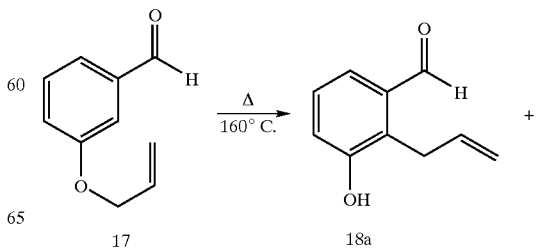

-continued

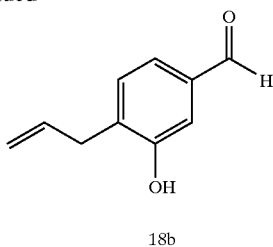

18b

In a 250 ml oven dry three neck-flash equipped with a condenser and thermometer was added 100 gms (0.617 mol) of allylether 17 under an atmosphere of argon. The mixture was heated slowly up to 150° C. (internal temperature), with temperature control monitored over the reaction period, on an oil bath (outside temp. 158° C.) and was left at this temperature for stirring for 41 hrs. After 41 hrs, the reaction mixture turned dark brown and becomes a thick slurry and at this point the TLC as well as NMR showed the maximum conversion of starting material to product (78–80%). At this stage, the reaction mixture was cooled down to room temperature and taken up in dichloromethane (1 L) and extracted twice with 10% sodium hydroxide solution (350 ml, 200 ml) (until there is no more product in the organic layer, as checked by TLC). The combined aqueous layers (10% NaOH) were neutralized with 25% HCl until the pH is 2, (determined by using pH paper) at this stage a crude brown solid separated in the aqueous layer and the resulting aqueous layer was extracted in dichloromethane (1.5 L×2, 500 ml×2). The combined organic layers were dried over sodium sulfate and evaporated in vacuo to yield a crude brown solid (77 gms) which was purified by flash chromatography using 230–400 mesh silica gel (396 gms) by slowly increasing the gradient of ethyl acetate (1%–10%) in hexanes. Fractions containing the required compound were evaporated to afford 40 gms of solid which was mixture of isomers 18a and 18b (ratio 2:4, by NMR) and the isomers were separated by recrystallization and NaHSO$_3$.

Separation of Isomers 18a and 18b:

(c)

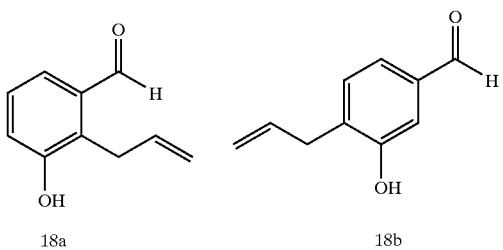

18a 18b

The compound obtained after the rearrangement of 17 to 18 was a mixture of isomers 18a and 18b in the ratio of 2:1, respectively. The crude yellow (40 gms) compound was first purified by recrystallization from dichloromethane (200 ml) and hexanes (400 ml) to yield a fluffy white solid (yield 29.5 gms) having isomers in the ratio of 5:1 (determined by NMR), respectively. To the 29.5 gms of the 5:1 mixture was added a solution of 3.60 gms of sodium bisulfite in 60 ml of water and the mixture was shaken vigorously for 5–8 minutes. After vigorous shaking, the mixture was filtered and washed with excess water (100 ml) to remove the soluble sodium bisulfite addition product of isomer 18b, leaving behind isomer 18a on the filtration funnel, which was dried and characterized by its spectral data. The NMR showed the presence of single isomer 18a and complete disappearance of isomer 18b; yield 25 gms, m.p. 107° C.: $^1$H NMR (CDCl$_3$): 3.89–3.92 (d, 2H, CH$_2$), 4.98–5.51 (m, 2H, =CH), 5.42 (brs, 1H, exchangeable with D$_2$O, OH), 5.97–6.11 (m, 1H, =CH), 7.08–7.11 (d, 1H, Ar 4H), 7.11–7.30 (d, 1H, Ar 5H), 7.44–7.47 (d, 1H, Ar 6H), 10.19 (s, 1H, CHO); HRMS calcd. for C$_{10}$H$_{10}$O$_2$ (M—NH$_4$) 180.1025, Found 180.1025; Anal. calcd. for C$_{10}$H$_{10}$O$_2$C, 74.07; H,6.17; Found: C, 74.07; H, 6.15.

Preparation of 2-Allyl-3-benzyloxybenzaldehyde 19:

(d)

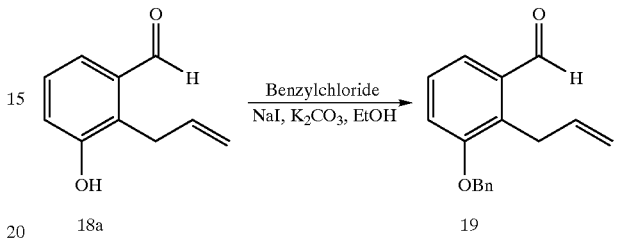

18a 19

To a stirred solution of 18a (1 gm, 0.006 mol) in 20 ml of 95% EtOH was added, at room temperature, NaI (89 mg, 10 mol %), K$_2$CO$_3$ (1.02 gm 0.0072 mol) and dropwise 0.909 gm (0.82 ml, 0.0072 mol) of benzyl chloride. The mixture was refluxed for 4–5 hrs (until completion of reaction as monitored by TLC) and the suspension was filtered and the filtrate was evaporated in vacuo to afford a crude solid compound (2 gm). The crude solid was dissolved in 30 ml of dichloromethane and washed with 20 ml of 10% NaOH solution. The aqueous layer was washed with 20 ml of dichloromethane and the combined organic layers were dried over sodium sulfate and reduced on vacuo to give solid (1.45 gm) which was crystallized from hexanes to yield 1.2 gm of pure solid compound 19; yield 80%, m.p. 66° C.–67° C., $^1$HNMR (CDCl$_3$): 3.99 (d 2H), 4.90–4.9 (m 2H), 5.05–5.13 (s, 2H), 5.9–6.1 (m 1H), 7.1–7.5 (m 8H); HRMS calcd for C$_{17}$H$_{40}$O$_2$ (M+H) 253.1226, found 253.1229; Anal. calcd for: C, 74.07; H, 6.17; Found: C, 74.07; H, 6.15.

Preparation of Diastereomeric benzylalkynol 20:

(e)

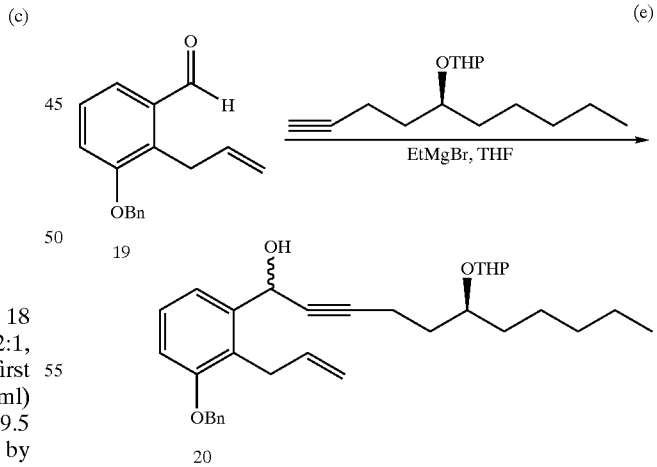

19

20

A solution of side chain A (S-1-decyn-O-tetrahydropyranyl-2-yl-5-ol) (10% pure, 1.4 gms, 1.1 eq, prepared using conventional techniques of organic chemistry) in anhydrous THF was taken up in a 50 ml flame dried three neck round bottom flask equipped with a condenser, magnetic bar and dropping funnel under argon. The reaction mixture was heated to gentle reflux (boiling at the boiling point of THF, about 65–67° C. and a solution of EtMgBr (0.512 gm, 4 ml, 1 M in THF) was added dropwise with stirring. After the complete addition the reaction mixture was refluxed for an additional 90 minutes then cooled and then a solution of 19 (970 mg, 0.0038 mol) in 15 ml dry THF was added dropwise. After the addition, the reaction mixture was allowed to warm to room temperature and left overnight with stirring (until completion of the reaction, monitored by TLC) and a solution of saturated ammonium chloride (10 ml) was added dropwise with stirring. The aqueous layer was extracted with ethyl acetate (2×20 ml). The combined organic layers were washed with brine, dried over $Na_2SO_4$ and the solvent was removed in vacuo. The crude viscous liquid was purified by flash chromatography using silica gel (230–400 mesh). A solvent gradient of 2–11% ethyl acetate in hexanes was used to elute the product from column. The fractions containing the desired compound were evaporated on vacuo to yield benzylalkynol 20 (1.5 gm, 80%), $^1$HNMR (CDCl$_3$): 0.88 (t, 3H), 1.27–1.81 (m, 17H), 2.26–2.44 (dt, 2H), 3.43–3.92 (m, 4H), 4.66–4.67 (d, 1H), 4.92–4.93 (m, 2H), 5.01–5.08 (m, 2H), 5.01–5.08 (m, 2H), 5.64 (s, 1H), 5.96–6.09 (m, 1H), 6.89–6.93 (d, 1H), 7.18–7.44 (m, 7H); HRMS calcd for $C_{32}H_{42}O_4$ (M+Na) 513.2971, Found: 513.2962; Anal. calcd for $C_{32}H_{42}O_4$, C, 78.36; H, 8.57; Found: C, 77.73, H, 8.80.

Preparation of Aryl alkynyl ketone 21:

(f)

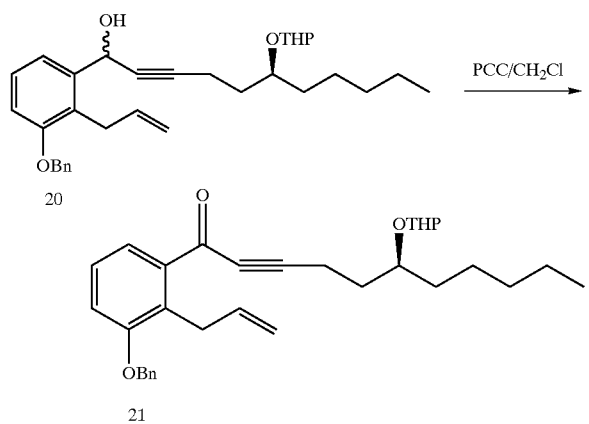

Benzyl alkynol 20 (0.870 gm, 0.0017 mol) was dissolved in dry dichloromethane (20 ml) in a three neck 50 ml round bottomed flask equipped with a thermometer, magnetic bar and argon inlet-outlet trap. It was cooled to 0° C. under argon and pyridinium chlorochromate (PCC, 0.765 gm, 0.0035 mol, 2 eq.) was added portionwise while stirring. The reaction mixture was slowly allowed to warm to ambient temperature and left with stirring under argon for approximately 12 hrs. (checked by TLC). The mixture was filtered through Celite (4 gm) using a Büchner funnel. The dark brown solid in the reaction flask and on the Büchner funnel was washed with ethyl acetate (2×10 ml). The solvent was removed in vacuo and the crude product was purified by column chromatography using 230–400 mesh silica gel. A solvent gradient of ethyl acetate in hexanes (2–5%) was used to elute the product from column. Fractions containing the desired compound were combined and concentrated in vacuo to yield aryl alkyl ketone 21 (0.600 gm, 69%) as a light yellow viscous liquid, $^1$HNMR (CDCl$_3$): 0.86 (t, 3H), 1.28–1.65 (m, 16H), 2.51 (t, H), 2.62 (t, 1H), 3.45–3.51 (m, 1H), 3.71–3.93 (m, 4H), 4.62–4.63 (m, 1H), 4.94–4.97 (m, 2H), 4.99–5.10 (m, 2H), 5.92–6.09 (m, 1H), 7.08–7.12 (d, 1H), 7.22–7.45 (m, 6H), 7.76 (t, 1H); HRMS exact mass calcd for $C_{32}H_{40}O_4$ (M+Na) 511.282, found 511.280, anal. calcd for: C, 78.69; H, 8.19; Found: C, 7.73; H, 8.34.

Preparation of Benzylalkynol 22:

(g)

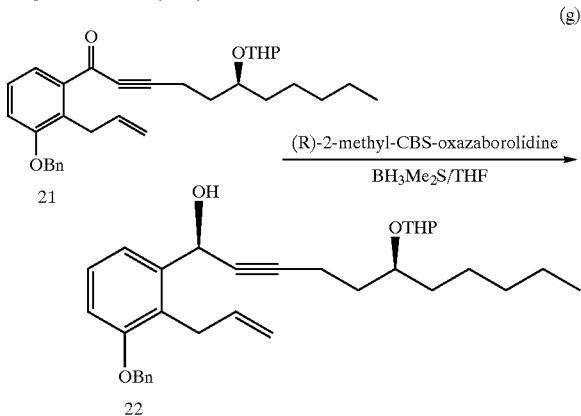

To a solution of aryl alkyl ketone 21 (3 gm, 0.00614 mol) in anhydrous tetrahydrofuran (40 ml) in 100 ml three neck round bottom flask was added a solution of (R)-D-methyl oxazaborolidine (2.04 gm, 7.36, 0.0065 mol, 1.2 eq, 1M solution in toluene) slowly over a period of one minute. The resulting solution was cooled to −30° C. under argon and borane-methylsulfide complex (0.700 gm, 4.6 ml, 0.092 mol, 1.5 eq, 2M solution in THF) was added dropwise with stirring. After the addition was complete (2 minutes), the reaction mixture was stirred at −40° C. to −30° C. for 2 hrs and the reaction was monitored by TLC. After completion, the reaction was quenched by dropwise addition of methanol (5–8 ml) at −40° C. The resulting solution was allowed to attain ambient temperature (leaving overnight with stirring). The reaction was cooled to 0–10° C. and 5% aqueous ammonium chloride (20 ml) was added with stirring. The mixture was stirred for 10 minutes and the organic layer was separated and filtered through Celite (5 gm). The filtrate was washed with 5% aqueous ammonium chloride (15 ml) and brine 20 ml). The combined aqueous layers were extracted with ethyl acetate (2×20 ml). The combined organic layers were dried over sodium sulfate and concentrated in vacuo to yield crude S-(+)-benzylalkynol as a yellow oil (2.78 gm). The crude viscous liquid was purified by column chromatography using 230–400 mesh silica gel. A solvent gradient of ethyl acetate in hexanes (4–10%) was used to elute the produce from column. The fractions containing the desired compound were evaporated in vacuo to yield chiral benzyalkynol 22, 1.80 gm (60%). $^1$HNMR (CDCl$_3$): 0.88 (t, 3H), 1.28–1.83 (m, 17H), 2.26–2.43 (m, 2H). 3.42–3.91 (m, 4H), 4.67 (d, 1H), 4.90–4.92 (m, 2H), 5.04–5.10 (m, 2H), 5.65 (m, 1H), 5.96–6.02 (m, 1H), 6.88–6.93 (d, 1H), 7.18–7.45 (m, 7H); anal. calcd for: C, 78.36; H, 8.57, Found: C, 77.87; H, 8.57.

Preparation of Benzyl alkynyl t-butyldimethylsilyl 23:

(h)

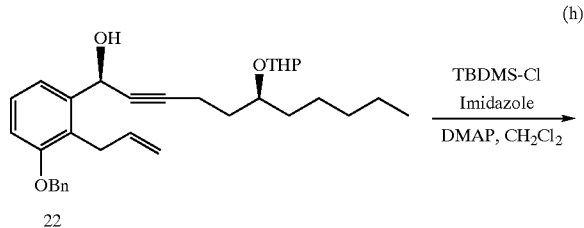

-continued

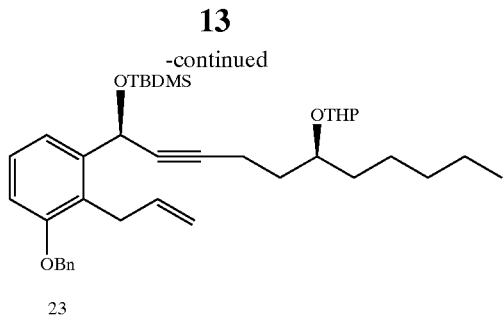

23

To a solution of chiral benzylalkynol 22 (2 gm, 0.00408 mol) in a three neck round bottom flask, in dichloromethane (50 ml) were added slowly imidazole (0.389 gm, 0.0057 mol), 4-(dimethylamino)pyridine (DMAP, 0.050 gm, 0.00040 mol) and DMF (10 ml) with stirring. The stirring continued until a clear solution was obtained. The mixture was cooled to 0° C. under argon and t-butyldimethylsilyl chloride (TBDMSCl, 0.918 gm, 0.0061 mol) was added slowly with stirring over a period of approximately 10 minutes. The reaction was slowly allowed to warm to ambient temperature and stirring was continued for approximately 15 hrs. (monitored by TLC). The crude mixture was washed with water (2×20 ml), brine (20 ml) and dried over sodium sulfate and concentrated in vacuo. The crude product was purified by column chromatography using 230–400 mesh silica gel and eluting with solvent gradient of ethyl acetate in hexanes (24%). The fractions containing the desired compound were evaporated in vacuo to yield benzyl alkynyl t-butyldimethylsilyl ether 23 (1.94 gm, 80%) IR (NaCl) Cm$^{-1}$: 2933, 2855, 1582, 1457, 1252, 1125; $^1$HNMR (CDCl$_3$): 0.10 (d, 6H), 0.73–0.95 (m, 12H), 1.27–1.77 (m, 16H), 2.17–2.37 (m, 2H), 3.41–3.86 (m, 5H), 4.584.61 (m, 1H), 4.92–4.96 (m, 2H), 5.10 (s, 2H), 5.92–6.02 (m, 1H), 6.85–6.9 (d, 1H), 7.15–7.47 (m, 7H); Anal. calcd for: C, 75.49; H, 9.27, Found: C, 74.87; H, 9.26.

Preparation of Tricyclic enone via catalytic Pauson-Khand cyclization 24:

(i)

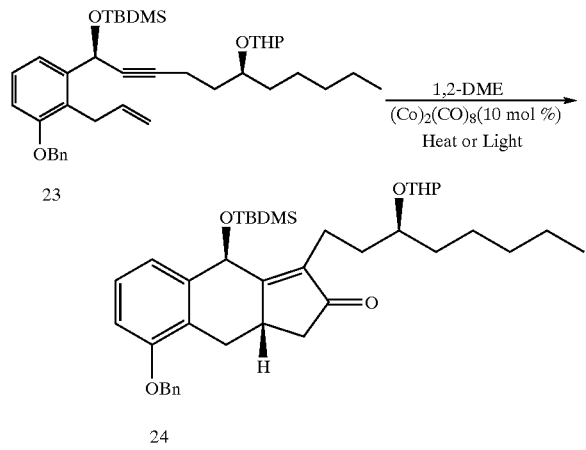

A solution of enyne 23 (1.35 gm, 0.0022 mol) and Co$_2$(CO)$_8$ (0.076 gm, 0.00022 mol, 10 mol %) in degassed 1,2-DME (was made free of oxygen by continuously bubbling with argon for 5 minutes, 35 ml) was magnetically stirred at room temperature under an atmosphere of carbon monoxide (CO, using balloon). After 30 minutes the reaction mixture was heated to 58–60° C. using constant oil bath for 15 hrs (until the reaction was complete. After cooling to room temperature, 1,2-DME (solvent) was evaporated in vacuo to yield crude gummy mass which was taken up in ethyl acetate (20 ml) and to this was added brine (15 ml) and organic layer containing the desired compound was extracted, dried over sodium sulfate and reduced under vacuo to afford an oily compound which was purified by flash chromatography on silica gel using 2–3% ethyl acetate in hexanes. Fractions containing the desired compound were collected and reduced under vacuo to yield 24, 1.02 gm, 73%; IR (NaCl) Cm$^{-1}$: 2933, 2853, 1698, 1651, 1579, 1455, 1248, 1033; $^1$HNMR (CDCl$_3$): 0.10 (m, 6H), 0.82–0.94 (m, 12H), 1.13–1.73 (m, 16H), 2.04–2.46 (m, 1H), 2.63–2.72 (dd, 1H) 3.33–3.66 (m, 4H), 4.55–4.56 (m, 1H), 5.05 (s, 2-H) 5.10 (s, 2H), 5.48–5.60 (two s, 1H), 1H), 6.82–6.96 (m, 2H), 7.18–7.42 (m, 6H); Anal. calcd for: C, 74.05; H, 8.86, Found: C, 73.42; H, 8.81.

Preparation of Tricyclic Ketone 25:

(j)

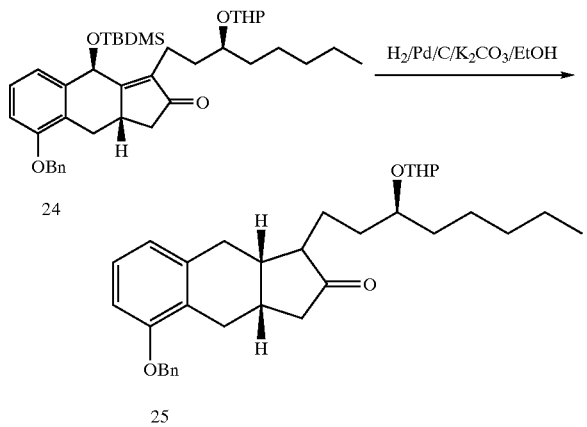

To a solution of tricyclic enone 24 (1 gm, 0.0015 mol) in absolute ethanol (50 ml) were added anhydrous K$_2$CO$_3$ (0.1 gm) and 10% Pd/C (0.4 gm, 50% wet) and the mixture was hydrogenated at 50–60 psi pressure for 7–8 hrs at room temperature (monitored by IR and TLC of reaction mixture every 2 hrs). The reaction mixture was filtered through Celite (5 gm). The Celite was washed with ethanol 20 ml and the filtrate was evaporated in vacuo to yield a crude oily compound which was further purified by flash chromatography using 230–400 mesh silica gel and solvent gradient of ethyl acetate and hexanes (10–35%). Fractions containing the required compound were evaporated in vacuo to yield tricyclic ketone 25, 0.384 gm (60%); IR (NaCl) Cm$^{-1}$: 3343, 2931, 2857, 1726, 1603, 1459, 1275, 1126; $^1$HNMR (CDCl$_3$): 0.88 (t, 3H), 1.21–1.51 (m, 6H), 1.52–2.10 (m, 6H), 2.13–3.10 (m, 7H), 3.48–3.64 (m, 2H), 3.88–3.93 (m, 1H), 4.63 (s, 1H) 5.96 (d, 1H) 6.61–6.72 (m, 2H), 6.95–7.04 (m, 1H); HRMS exact mass calcd for C$_{26}$H$_{38}$O$_4$ (M+Na) 437.26693, Found 437.26642.

Preparation of Tricyclic alcohol 26:

(k)

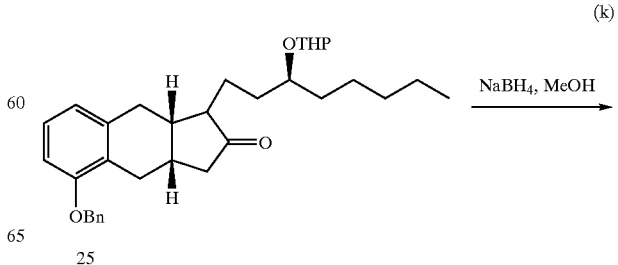

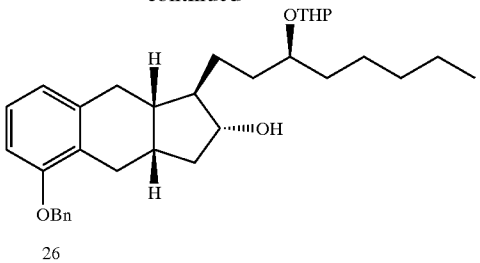

26

A two neck 50 ml round bottom flask equipped with a thermometer and magnetic bar was charged with a solution of tricyclic ketone 25 (0.202 gm, 0.00048 mol) in ethanol (20 ml). It was cooled to −10° C. (the temperature was maintained by using mixture of ethylene glycol and dry ice) and 10% NaOH solution (0.1 ml) was added with stirring under argon. The reaction mixture was stirred for 15 minutes and then NaBH$_4$ (0.017 gm, 0.00048 mol, 1 eq.) was added and stirring continued at −10° C. for 1 hr. An additional equivalent of NaBH$_4$ (0.017 gm, 0.00048 mol, 1 eq) was added and stirring continued for another 6 hrs at −10° C. (progress of reaction was checked by TLC). The reaction mixture was quenched carefully with glacial acetic acid (2–3 ml until pH was 5–6) at −10° C. The reaction mixture was allowed to attain room temperature (left overnight), diluted with water (10 ml) and the solvent was removed in vacuo. The crude reaction mixture was dissolved in ethyl acetate (25 ml) washed with aq. NaHCO$_3$ (2×10 ml), brine (10 ml) and dried over sodium sulfate and concentrated in vacuo to obtain crude oily tricyclic alcohol. Further purification was done by using flash chromatography (230–400 mesh silica gel) under solvent gradient of ethyl acetate in hexanes to obtain tricyclic alcohol 26, 0.140 gm (69.3%); IR (NaCl) Cm$^{-1}$: 3349, 2931, 2859, 1586, 1461, 1348, 1280, 1020; $^1$HNMR (CDCl$_3$): 0.88 (t, 3H), 1.21–1.27 (q, 2H), 1.47–1.48 (m, 6H), 1.52–1.72 (m, 1H), 1.73–1.86 (m, 3H), 1.87–2.13 (m, 2H) 2.15–2.47 (m, 2H), 2.66–2.73 (m, 2H), 3.47–3.50 (m, 1H), 3.71–3.74 (m, 2H), 3.92–3.96 (m, 1H), 4.60–4.61 (d, 1H) 5.78 (brs, 1H) 6.61–6.63 (m, 1H), 6.64–6.70 (m, 1H), 6.93–6.98 (m, 1H); HRMS exact mass calcd for C$_{26}$H$_{40}$O$_4$ (M+Na) 439.2826, Found 439.2816.

Preparation of Benzindene triol 15:

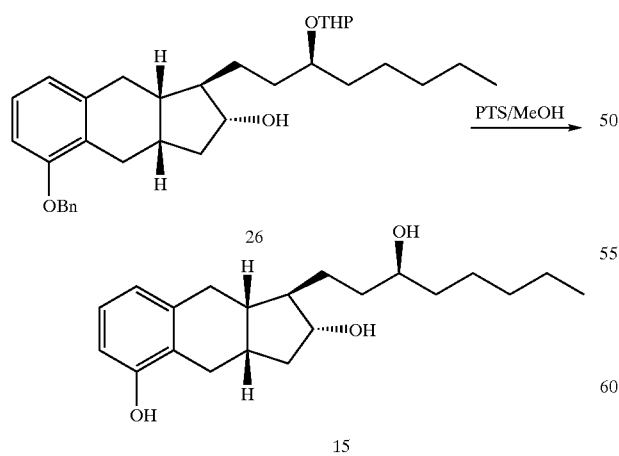

To a solution of tricyclic alcohol 26 (0.124 gm, 0.00029 mol) in methanol (16 ml) at 0° C. under argon was added p-toluenesulfonic acid monohydrate (0.006 gm, 10 mol %) with stirring. The reaction mixture was stirred and slowly warmed to room temperature for 15 hrs (reaction monitored by TLC). The solvent was evaporated in vacuo and the crude product was purified by flash chromatography using 230–400 mesh silica gel. A solvent gradient of 10–50% ethyl acetate in hexanes was used to elute the product from column. The fractions containing compound 15 were evaporated in vacuo to give benzindene triol 15 (0.079 gm, 80%), m.p. 116–18° C. (lit. (2) m.p. 114–17° C., compared with the melting of authentic sample obtained from UT-15 synthesis); IR (NaCl) Cm$^{-1}$: 3336, 2922, 2853, 1582, 1459, 1276; $^1$HNMR (CDCl$_3$): 0.89 (t, 3H), 1.10–2.27 (m, 1H), 242–2.47 (m, 2H), 2.49–2.73 (m, 2H), 3.61 (brs, 1H), 3.70–3.76 (m, 1H), 5.27 (brs, 1H), 6.65 (d, 1H), 6.73 (d, 1H), 6.98 (m, 1H).

It will be apparent to those skilled in the art that various modifications and variations can be made to the processes and novel intermediates of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually.

What is claimed is:

1. A process for making 9-deoxy-PGF$_1$-type compounds comprising:
   (a) intramolecular enyne cyclization of a starting compound of the formula:

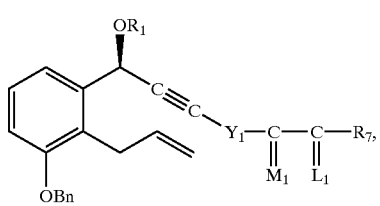

accompanied by
   (b) carbon monoxide insertion; to form a tricyclic compound of the following formula:

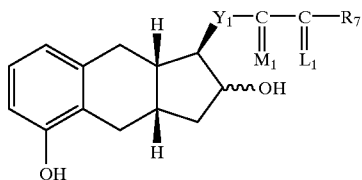

wherein Y$_1$ is trans-CH=CH—, cis-CH=CH—, —CH$_2$(CH$_2$)$_m$—, or —C≡C—; m is 1,2, or 3;
wherein R$_1$ is H or an alcohol protecting group;
wherein R$_7$ is
   (1) —C$_p$H$_{2p}$—CH$_3$, wherein p is an integer from 1 to 5, inclusive,
   (2) phenoxy optionally substituted by one, two or three chloro, fluoro, trifluoromethyl, (C$_1$–C$_3$) alkyl, or (C$_1$–C$_3$)alkoxy, with the proviso that not more than two substituents are other than alkyl, with the proviso that R$_7$ is phenoxy or substituted phenoxy, only when R$_3$ and R$_4$ are hydrogen or methyl, being the same or different,
   (3) phenyl, benzyl, phenylethyl, or phenylpropyl optionally substituted on the aromatic ring by one, two or three chloro, fluoro, trifluoromethyl, (C$_1$–C$_3$)alkyl, or (C$_1$–C$_3$)alkoxy, with the proviso that not more than two substituents are other than alkyl, (4) cis-CH=CH—$CH_2$-$CH_3$,
(5) —$(CH_2)_2$—CH(OH)—$CH_3$, or
(6) —$(CH_2)_3$—CH=$C(CH_3)_2$;
wherein —C($L_1$)—$R_7$ taken together is
(1) ($C_4$-$C_7$)cycloalkyl optionally substituted by 1 to 3 ($C_1$-$C_5$)alkyl;
(2) 2-(2-furyl)ethyl,
(3) 2-(3-thienyl)ethoxy, or
(4) 3-thienyloxymethyl;
wherein $M_1$ is α-OH:β-$R_5$ or α-$R_5$:β-OH or α-$OR_1$:β-$R_5$ or α-$R_5$:β-$OR_1$, wherein $R_5$ is hydrogen or methyl and $R_1$ is an alcohol protecting group; and
wherein $L_1$ is α-$R_3$:β-$R_4$, α-$R_4$:β-$R_3$, or a mixture of α-$R_3$:β-$R_4$ and α-$R_4$:β-$R_3$, wherein $R_3$ and $R_4$ are hydrogen, methyl, or fluoro, being the same or different, with the proviso that one of $R_3$ and $R_4$ is fluoro only when the other is hydrogen or fluoro.

2. The process as claimed in claim 1, wherein the cyclization is a cobalt-mediated cyclization.

3. The process as claimed in claim 2, wherein the starting compound is reacted with $Co_2(CO)_8$ in a non-reactive solvent to form a complex.

4. The process as claimed in claim 3, wherein the non-reactive solvent during the complex-forming step is 1,2-DME.

5. A stereoselective process of making a 9-deoxy-$PGF_1$-type compound, comprising the following reaction:

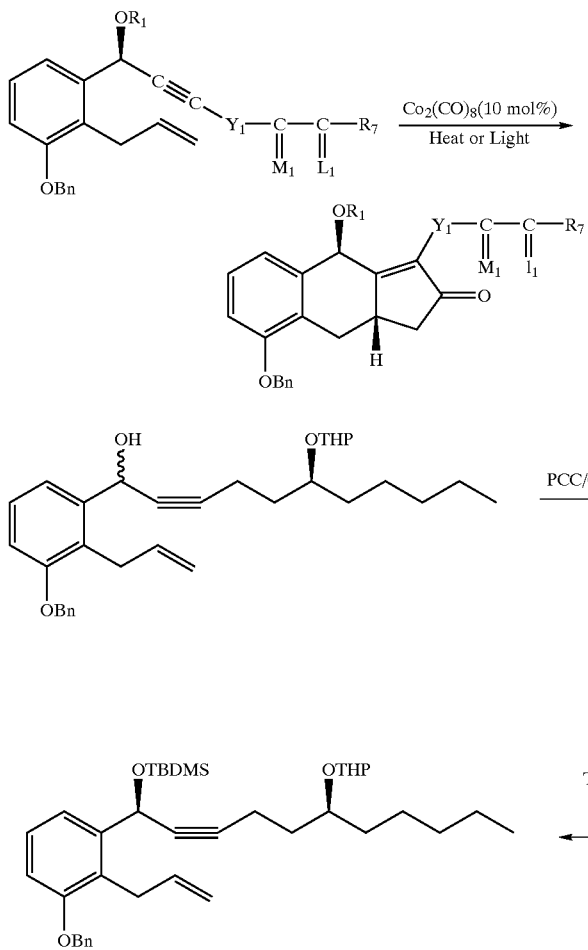

wherein $R_1$ is an alcohol protecting group;

wherein n is 0, 1, 2, or 3;

wherein $Y_1$ is trans-CH=CH—, cis-CH=CH—, —$CH_2$$(CH_2)_m$—, or —C≡C—; m is 1, 2, or 3;

wherein $R_7$ is
(1) —$C_pH_{2p}$—$CH_3$, wherein p is an integer from 1 to 5, inclusive,
(2) phenoxy optionally substituted by one, two or three chloro, fluoro, trifluoromethyl, ($C_1$-$C_3$)alkyl, or ($C_1$-$C_3$)alkoxy, with the proviso that not more than two substituents are other than alkyl, with the proviso that $R_7$ is phenoxy or substituted phenoxy, only when $R_3$ and $R_4$ are hydrogen or methyl, being the same or different,
(3) phenyl, benzyl, phenylethyl, or phenylpropyl optionally substituted on the aromatic ring by one, two or three chloro, fluoro, trifluoromethyl, ($C_1$-$C_3$) alkyl, or ($C_1$-$C_3$)alkoxy, with the proviso that not more than two substituents are other than alkyl,
(4) cis-CH=CH—$CH_2$—$CH_3$,
(5) —$(CH_2)_2$—CH(OH)—$CH_3$, or
(6) —$(CH_2)_3$—CH=$C(CH_3)_2$;

wherein —C($L_1$)—$R_7$ taken together is
(1) ($C_4$-$C_7$)cycloalkyl optionally substituted by 1 to 3 ($C_1$-$C_5$)alkyl;
(2) 2-(2-furyl)ethyl,
(3) 2-(3-thienyl)ethoxy, or
(4) 3-thienyloxymethyl;

wherein $M_1$ is α-OH:β-$R_5$ or α-$R_5$:β-OH or α-$OR_1$:β-R or α-$R_5$:β-$OR_1$, wherein $R_5$ is hydrogen or methyl and $R_1$ is an alcohol protecting group;

wherein $L_1$ is α-$R_3$:β-$R_4$, α-$R_4$:β-$R_3$, or a mixture of α-$R_3$:β-$R_4$ and α-$R_4$:β-$R_3$, wherein $R_3$ and $R_4$ are hydrogen, methyl, or fluoro, being the same or different, with the proviso that one of $R_3$ and $R_4$ is fluoro only when the other is hydrogen or fluoro.

6. The process as claimed in claim 1, further comprising the following steps:

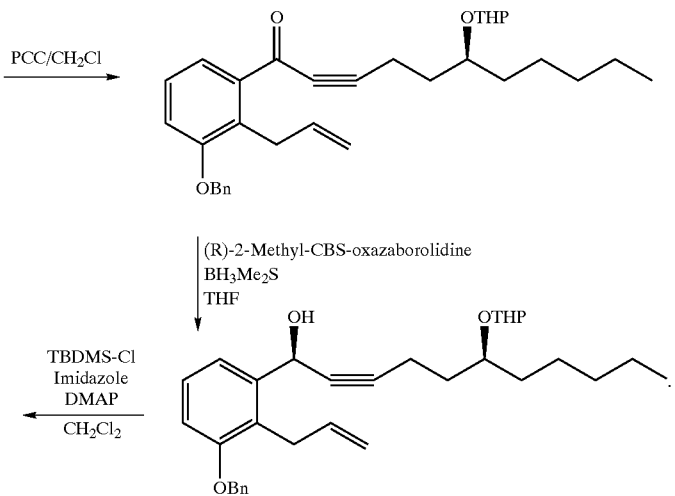

7. The process as claimed in claim 6, comprising the following steps:

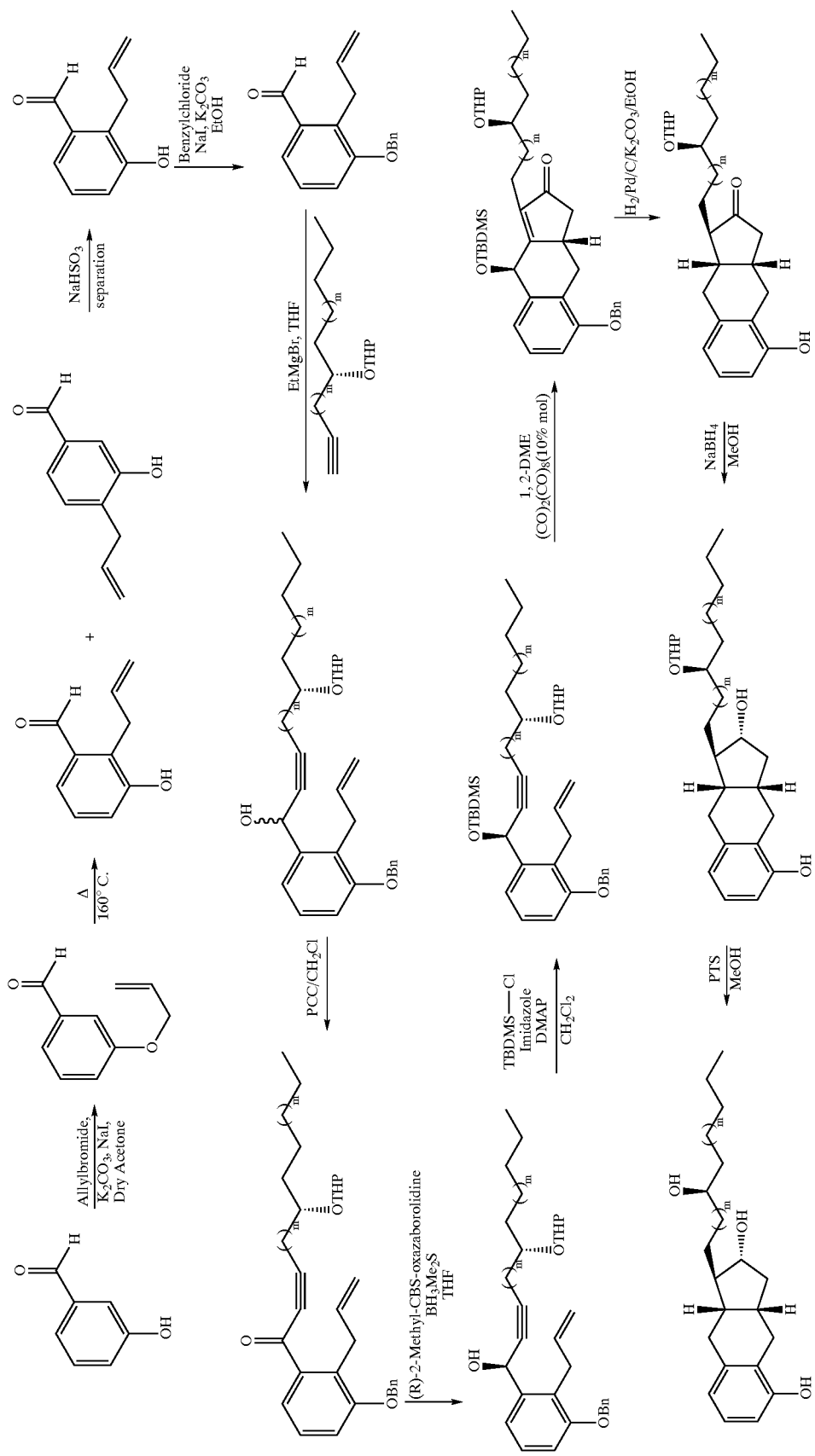

wherein m is 1, 2, or 3.

8. The process as claimed in claim 7, wherein m is 1.

9. A compound of the formula

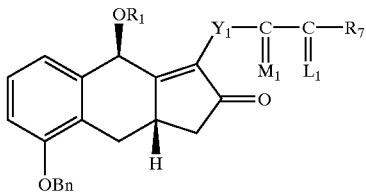

wherein $R_1$ is an alcohol protecting group;

wherein $Y_1$ is trans-CH=CH—, cis-CH=CH—, —CH$_2$(CH$_2$)$_m$—, or —C≡C—; m is 1, 2, or 3;

wherein $R_7$ is
  (1) —$C_pH_{2p}$—CH$_3$, wherein p is an integer from 1 to 5, inclusive,
  (2) phenoxy optionally substituted by one, two or three chloro, fluoro, trifluoromethyl, ($C_1$–$C_3$)alkyl, or ($C_1$–$C_3$)alkoxy, with the proviso that not more than two substituents are other than alkyl, with the proviso that $R_7$ is phenoxy or substituted phenoxy, only when $R_3$ and $R_4$ are hydrogen or methyl, being the same or different,
  (3) phenyl, benzyl, phenylethyl, or phenylpropyl optionally substituted on the aromatic ring by one, two or three chloro, fluoro, trifluoromethyl, ($C_1$–$C_3$)alkyl, or ($C_1$–$C_3$)alkoxy, with the proviso that not more than two substituents are other than alkyl,
  (4) cis-CH=CH—CH$_2$—CH$_3$,
  (5) —(CH)$_2$—CH(OH)—CH$_3$, or
  (6) —(CH)$_3$—CH=C(CH$_3$)$_2$;

wherein —C($L_1$)—$R_7$ taken together is
  (1) ($C_4$–$C_7$)cycloalkyl optionally substituted by 1 to 3 ($C_1$–$C_5$)alkyl;
  (2) 2-(2-furyl)ethyl,
  (3) 2-(3-thienyl)ethoxy, or
  (4) 3-thienyloxymethyl;

wherein $M_1$ is α-OH:β-$R_5$ or α-$R_5$:β-OH or α-$OR_1$:β-$R_5$ or α-$R_5$:β-$OR_1$, wherein $R_5$ is hydrogen or methyl and $R_1$ is an alcohol protecting group;

wherein $L_1$ is α-$R_3$:β-$R_4$, α-$R_4$:β-$R_3$, or a mixture of α-$R_3$:β-$R_4$ and α-$R_4$:β-$R_3$, wherein $R_3$ and $R_4$ are hydrogen, methyl, or fluoro, being the same or different, with the proviso that one of $R_3$ and $R_4$ is fluoro only when the other is hydrogen or fluoro.

10. A stereoselectively produced isomeric compound according to the following formula:

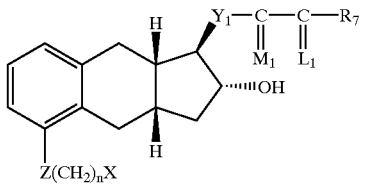

wherein Z is O, X is H, n is 0, and $Y_1$, $M_1$, $L_1$, and $R_7$ are as defined in claim 1 and said compound is produced according to the stereoselective synthesis of claim 1.

11. The stereoselectively produced isomeric compound of claim 10, wherein $Y_1$ is —CH$_2$CH$_2$—$M_1$ is α-OH:β-$R_5$, wherein $R_5$ is hydrogen, $L_1$ is α-$R_3$:β-$R_4$, wherein $R_3$ and $R_4$ are hydrogen and $R_7$ is propyl.

12. The stereoselectively produced compound of claim 10, which is produced as a pure diasteromer.

13. A stereoselective process of preparing a 9-deoxy-$PGF_1$-type compound, comprising:

(a) intramolecular cyclization of an enyne of the formula:

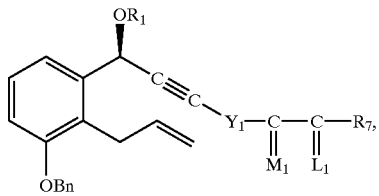

accompanied by (b) carbon monoxide insertion;

wherein $R_1$ is an alcohol protecting group;

wherein $Y_1$ is trans-CH=CH—, cis-CH=CH—, —CH$_2$(CH$_2$)$_m$—, or —C≡C—; m is 1,2, or 3;

wherein $R_7$ is
  (1) —$C_pH_{2p}$—CH$_3$, wherein p is an integer from 1 to 5, inclusive,
  (2) phenoxy optionally substituted by one, two or three chloro, fluoro, trifluoromethyl, ($C_1$–$C_3$) alkyl, or ($C_1$–$C_3$)alkoxy, with the proviso that not more than two substituents are other than alkyl, with the proviso that $R_7$ is phenoxy or substituted phenoxy, only when $R_3$ and $R_4$ are hydrogen or methyl, being the same or different,
  (3) phenyl, benzyl, phenylethyl, or phenylpropyl optionally substituted on the aromatic ring by one, two or three chloro, fluoro, trifluoromethyl, ($C_2$–$C_3$)alkyl, or ($C_1$–$C_3$)alkoxy, with the proviso that not more than two substituents are other than alkyl,
  (4) cis-CH=CH—CH$_2$—CH$_3$,
  (5) —(CH$_2$)$_2$—CH(OH)—CH$_3$, or
  (6) —(CH$_2$)$_3$—CH=C(CH$_3$)$_2$;

wherein —C($L_1$)—$R_7$ taken together is
  (1) ($C_4$–$C_7$)cycloalkyl optionally substituted by 1 to 3 ($C_1$–$C_5$)alkyl;
  (2) 2-(2-furyl)ethyl,
  (3) 2-(3-thienyl)ethoxy, or
  (4) 3-thienyloxymethyl;

wherein $M_1$ is α-OH:β-$R_5$ or α-$R_5$:β-OH or α-$OR_1$:β-$R_5$ or α-$R_5$:β-$OR_1$, wherein $R_5$ is hydrogen or methyl and $R_1$ is an alcohol protecting group;

wherein $L_1$ is α-$R_3$:β-$R_4$, α-$R_4$:β-$R_3$, or a mixture of α-$R_3$:β-$R_4$ and α-$R_4$:β-$R_3$, wherein $R_3$ and $R_4$ are hydrogen, methyl, or fluoro, being the same or different, with the proviso that one of $R_3$ and $R_4$ is fluoro only when the other is hydrogen or fluoro;

to yield a compound of the formula:

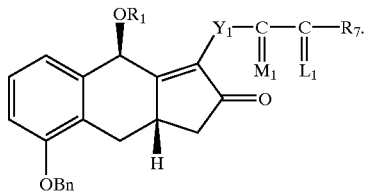

* * * * *